United States Patent
Simpson

(10) Patent No.: US 9,693,701 B2
(45) Date of Patent: Jul. 4, 2017

(54) ELECTRODE CONNECTOR DESIGN TO AID IN CORRECT PLACEMENT

(71) Applicant: Covidien LP, Mansfield, MA (US)

(72) Inventor: Robert Simpson, Holliston, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/209,278

(22) Filed: Mar. 13, 2014

(65) Prior Publication Data

US 2014/0275927 A1    Sep. 18, 2014

Related U.S. Application Data

(60) Provisional application No. 61/793,284, filed on Mar. 15, 2013.

(51) Int. Cl.
*A61B 5/04* (2006.01)
*A61B 5/0408* (2006.01)
*A61N 1/05* (2006.01)
*A61B 5/0416* (2006.01)

(52) U.S. Cl.
CPC .......... *A61B 5/0408* (2013.01); *A61B 5/0416* (2013.01); *A61N 1/05* (2013.01); *A61B 5/04085* (2013.01); *A61B 2562/0209* (2013.01)

(58) Field of Classification Search
USPC ................................................. 600/508–509
See application file for complete search history.

(56) References Cited

U.S. PATENT DOCUMENTS

| | | | |
|---|---|---|---|
| 3,606,881 A | 9/1971 | Woodson | |
| 3,752,151 A | 8/1973 | Robichaud | |
| 3,805,769 A | 4/1974 | Sessions | |
| 3,828,766 A | 8/1974 | Krasnow | |
| 3,829,826 A | 8/1974 | Brown et al. | |
| 3,842,394 A | 10/1974 | Bolduc | |
| 3,868,946 A | 3/1975 | Hurley | |
| 3,888,240 A | 6/1975 | Reinhold, Jr. et al. | |
| 3,895,635 A | 7/1975 | Justus et al. | |

(Continued)

FOREIGN PATENT DOCUMENTS

| CN | 1853247 A | 10/2006 |
|---|---|---|
| CN | 101219047 A | 7/2008 |

(Continued)

OTHER PUBLICATIONS

Notice of Allowance dated May 15, 2015 corresponding to U.S. Appl. No. 29/486,095; 25 Pages.

(Continued)

*Primary Examiner* — Nicole F Johnson

(74) *Attorney, Agent, or Firm* — Blaine A. Page, Esq.

(57) ABSTRACT

An electrode connector includes a housing, an electrically conductive contact plate, a lead wire terminal electrically connected to the contact plate and an electrically conductive member. The housing defines a first opening configured to receive at least a portion of an electrode therethrough. The contact plate defines a bore aligned with the first opening. The bore is configured and dimensioned to receive at least a portion of the electrode therein. The electrically conductive member is electrically coupled to the lead wire terminal. The electrically conductive member is supported on the housing and is spaced apart from the first opening.

14 Claims, 9 Drawing Sheets

(56) References Cited

U.S. PATENT DOCUMENTS

| | | |
|---|---|---|
| 3,901,218 A | 8/1975 | Buchalter |
| 3,997,225 A | 12/1976 | Horwinski |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,112,941 A | 9/1978 | Larimore |
| 4,144,889 A | 3/1979 | Tyers et al. |
| 4,166,465 A | 9/1979 | Esty et al. |
| 4,220,390 A | 9/1980 | Cobaugh et al. |
| 4,303,293 A | 12/1981 | Grunwald |
| D263,167 S | 2/1982 | Stone |
| 4,353,372 A | 10/1982 | Ayer |
| 4,365,634 A | 12/1982 | Bare et al. |
| 4,498,480 A | 2/1985 | Mortensen |
| 4,674,817 A | 6/1987 | Olms |
| 4,729,377 A | 3/1988 | Granek et al. |
| 4,763,660 A | 8/1988 | Kroll et al. |
| 4,781,200 A | 11/1988 | Baker |
| 4,785,822 A | 11/1988 | Wallace |
| 4,815,964 A | 3/1989 | Cohen et al. |
| 4,842,557 A | 6/1989 | Muz |
| 4,850,356 A | 7/1989 | Heath |
| 4,909,260 A | 3/1990 | Salem et al. |
| 4,947,846 A | 8/1990 | Kitagawn et al. |
| 4,957,109 A | 9/1990 | Groeger et al. |
| 4,974,594 A | 12/1990 | Berlin |
| 5,080,604 A | 1/1992 | Rider et al. |
| 5,083,238 A | 1/1992 | Bousman |
| 5,083,933 A | 1/1992 | Colleran et al. |
| 5,104,253 A | 4/1992 | Zielinski et al. |
| 5,104,334 A | 4/1992 | Honma et al. |
| 5,131,854 A | 7/1992 | Jose et al. |
| 5,137,466 A | 8/1992 | Endo et al. |
| 5,154,646 A | 10/1992 | Shoup |
| 5,158,469 A | 10/1992 | Martin |
| 5,160,276 A | 11/1992 | Marsh et al. |
| 5,173,059 A | 12/1992 | Sato et al. |
| 5,176,343 A | 1/1993 | Cheney et al. |
| 5,178,556 A | 1/1993 | Chen |
| 5,180,312 A | 1/1993 | Martin |
| 5,190,467 A | 3/1993 | Ohta |
| 5,192,226 A | 3/1993 | Wang |
| 5,197,901 A | 3/1993 | Hashiguchi |
| 5,199,897 A | 4/1993 | Hashiguchi |
| 5,201,669 A | 4/1993 | Lin |
| 5,203,715 A | 4/1993 | Yamamoto |
| 5,203,719 A | 4/1993 | Kozono |
| 5,207,594 A | 5/1993 | Olson |
| 5,224,479 A | 7/1993 | Sekine |
| 5,232,383 A | 8/1993 | Barnick |
| 5,234,357 A | 8/1993 | Yamaguchi |
| 5,243,510 A | 9/1993 | Cheney |
| 5,263,481 A | 11/1993 | Axelgaard |
| 5,276,443 A | 1/1994 | Gates et al. |
| 5,278,759 A | 1/1994 | Berra et al. |
| 5,279,308 A | 1/1994 | DiSabito et al. |
| 5,293,013 A | 3/1994 | Takahashi |
| 5,320,621 A | 6/1994 | Gordon et al. |
| 5,326,272 A | 7/1994 | Harhen et al. |
| 5,332,330 A | 7/1994 | Kaneko |
| 5,338,219 A | 8/1994 | Hiramoto |
| 5,341,806 A | 8/1994 | Gadsby et al. |
| 5,341,812 A | 8/1994 | Allaire et al. |
| 5,353,793 A | 10/1994 | Bornn |
| 5,354,216 A | 10/1994 | Cruise et al. |
| 5,362,249 A | 11/1994 | Carter |
| 5,370,116 A | 12/1994 | Rollman et al. |
| 5,370,550 A | 12/1994 | Alwine et al. |
| 5,376,016 A | 12/1994 | Inaba et al. |
| 5,378,168 A | 1/1995 | Sumida |
| 5,380,223 A | 1/1995 | Marsh et al. |
| 5,382,176 A | 1/1995 | Norden |
| 5,383,794 A | 1/1995 | Davis et al. |
| 5,387,116 A | 2/1995 | Wang |
| 5,387,127 A | 2/1995 | Wang |
| 5,399,045 A | 3/1995 | Yoneda et al. |
| 5,403,353 A | 4/1995 | Alferness et al. |
| 5,405,269 A | 4/1995 | Stupecky |
| 5,415,164 A | 5/1995 | Faupel et al. |
| 5,429,526 A | 7/1995 | Ann |
| 5,431,166 A | 7/1995 | Macur |
| 5,454,739 A | 10/1995 | Strand |
| 5,462,448 A | 10/1995 | Kida et al. |
| 5,484,739 A | 1/1996 | Lee et al. |
| 5,486,117 A | 1/1996 | Chang |
| 5,507,290 A | 4/1996 | Kelly et al. |
| 5,507,665 A | 4/1996 | Oda |
| 5,507,668 A | 4/1996 | Lambrinos et al. |
| 5,509,822 A | 4/1996 | Negus et al. |
| 5,511,553 A | 4/1996 | Segalowitz |
| 5,546,950 A | 8/1996 | Schoeckert et al. |
| 5,558,535 A | 9/1996 | Saka et al. |
| 5,564,939 A | 10/1996 | Maitani et al. |
| 5,582,180 A | 12/1996 | Manset et al. |
| 5,584,719 A | 12/1996 | Tsuji et al. |
| D377,219 S | 1/1997 | Strand et al. |
| 5,599,199 A | 2/1997 | Wright |
| 5,603,632 A | 2/1997 | Johannes et al. |
| 5,611,708 A | 3/1997 | Mizunuma et al. |
| 5,613,870 A | 3/1997 | Traver, Jr. |
| 5,615,674 A | 4/1997 | Maurer |
| 5,622,168 A | 4/1997 | Keusch et al. |
| 5,624,271 A | 4/1997 | Childs et al. |
| 5,624,281 A | 4/1997 | Christensson |
| 5,626,135 A | 5/1997 | Sanfilippo |
| 5,632,274 A | 5/1997 | Quedens et al. |
| 5,651,689 A | 7/1997 | Plyler et al. |
| 5,653,606 A | 8/1997 | Chrysostomou |
| 5,674,088 A | 10/1997 | Roche et al. |
| 5,676,694 A | 10/1997 | Boser et al. |
| 5,679,022 A | 10/1997 | Cappa |
| 5,679,029 A | 10/1997 | Saunier et al. |
| 5,685,303 A | 11/1997 | Rollman et al. |
| 5,695,355 A | 12/1997 | Hasenfratz et al. |
| 5,702,265 A | 12/1997 | Yamaguchi |
| 5,704,351 A | 1/1998 | Mortara et al. |
| 5,711,684 A | 1/1998 | Inoue et al. |
| 5,718,596 A | 2/1998 | Inaba et al. |
| 5,724,025 A | 3/1998 | Tavori |
| 5,724,984 A | 3/1998 | Arnold et al. |
| 5,725,525 A | 3/1998 | Kordis |
| 5,741,155 A | 4/1998 | Herman |
| 5,749,746 A | 5/1998 | Tan et al. |
| 5,769,650 A | 6/1998 | Aoyama et al. |
| 5,772,591 A | 6/1998 | Cram |
| 5,775,953 A | 7/1998 | Yamanashi et al. |
| 5,782,647 A | 7/1998 | Okura et al. |
| 5,782,761 A | 7/1998 | Gusakov |
| 5,782,892 A | 7/1998 | Castle et al. |
| 5,788,527 A | 8/1998 | Sanders et al. |
| 5,791,918 A | 8/1998 | Pierce |
| 5,797,854 A | 8/1998 | Hedgecock |
| 5,806,152 A | 9/1998 | Saitou et al. |
| 5,810,806 A | 9/1998 | Ritchart et al. |
| 5,813,404 A | 9/1998 | Devlin et al. |
| 5,813,979 A | 9/1998 | Wolfer |
| 5,827,086 A | 10/1998 | Fukuda |
| 5,830,000 A | 11/1998 | Shifflett et al. |
| 5,836,783 A | 11/1998 | Morisawa et al. |
| 5,843,141 A | 12/1998 | Bischoff et al. |
| 5,848,456 A | 12/1998 | Sjoqvist |
| 5,865,740 A | 2/1999 | Kelly et al. |
| 5,865,741 A | 2/1999 | Kelly et al. |
| 5,871,451 A | 2/1999 | Unger et al. |
| 5,873,747 A | 2/1999 | Tsuji |
| 5,876,232 A | 3/1999 | Matsushita et al. |
| 5,895,284 A | 4/1999 | Kocher et al. |
| 5,895,298 A | 4/1999 | Faupel |
| 5,904,579 A | 5/1999 | McLean et al. |
| 5,913,834 A | 6/1999 | Francais |
| 5,916,159 A | 6/1999 | Kelly et al. |
| 5,931,689 A | 8/1999 | Patel |
| 5,931,861 A | 8/1999 | Werner et al. |

(56) References Cited

U.S. PATENT DOCUMENTS

| | | |
|---|---|---|
| 5,934,926 A | 8/1999 | Gabrisko, Jr. et al. |
| 5,937,950 A | 8/1999 | Adams et al. |
| 5,938,470 A | 8/1999 | Kashiyama |
| 5,938,597 A | 8/1999 | Stratbucker |
| 5,941,725 A | 8/1999 | Brennan et al. |
| 5,944,562 A | 8/1999 | Christensson |
| 5,951,316 A | 9/1999 | Kawano et al. |
| 5,964,624 A | 10/1999 | Pernelle |
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,006,125 A | 12/1999 | Kelly et al. |
| 6,027,359 A | 2/2000 | Aoki et al. |
| 6,032,063 A | 2/2000 | Hoar et al. |
| 6,032,064 A | 2/2000 | Devlin et al. |
| 6,038,479 A | 3/2000 | Werner et al. |
| 6,038,481 A | 3/2000 | Werner et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,190,385 B1 | 2/2001 | Tom et al. |
| 6,203,354 B1 | 3/2001 | Kuwahara et al. |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,312,297 B1 | 11/2001 | Lorkowski |
| 6,324,432 B1 | 11/2001 | Rigaux et al. |
| D452,318 S | 12/2001 | Merry et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,363,272 B1 | 3/2002 | Combs |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,445,955 B1 | 9/2002 | Michelson et al. |
| 6,447,170 B1 | 9/2002 | Takahashi et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisander |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B2 | 8/2003 | Lin |
| 6,607,397 B1 | 8/2003 | Zhang et al. |
| 6,609,018 B2 | 8/2003 | Cory et al. |
| 6,609,833 B2 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wi |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,709,284 B2 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |

(56) References Cited

U.S. PATENT DOCUMENTS

| | | |
|---|---|---|
| D498,535 S | 11/2004 | Genau et al. |
| 6,816,744 B2 | 11/2004 | Garfield et al. |
| 6,832,928 B2 | 12/2004 | Suzuki et al. |
| 6,837,734 B2 | 1/2005 | Ushlo et al. |
| 6,847,836 B1 | 1/2005 | Sujdak |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | KenKnight et al. |
| 6,945,796 B2 | 9/2005 | Bassler et al. |
| 6,945,807 B1 | 9/2005 | Wu |
| 6,948,973 B1 | 9/2005 | Hsu et al. |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 6,984,143 B2 | 1/2006 | Roese |
| D516,217 S | 2/2006 | Brown et al. |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,077,711 B1 | 7/2006 | Moore |
| 7,081,008 B2 | 7/2006 | Tan |
| 7,081,026 B2 | 7/2006 | Schwarz |
| 7,083,480 B2 | 8/2006 | Silber |
| 7,085,598 B2 | 8/2006 | Sato |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,150,655 B2 | 12/2006 | Mastrototaro et al. |
| D535,029 S | 1/2007 | McAtamney et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | Le Gallic et al. |
| 7,214,107 B2 | 5/2007 | Powell et al. |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,255,609 B1 | 8/2007 | Epstein |
| 7,258,565 B2 | 8/2007 | Huang et al. |
| 7,258,566 B2 | 8/2007 | Koenig et al. |
| 7,264,510 B2 | 9/2007 | Koenig et al. |
| 7,270,568 B2 | 9/2007 | Osypka |
| 7,270,580 B2 | 9/2007 | Bradley et al. |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillinville et al. |
| 7,322,849 B2 | 1/2008 | Sutton |
| 7,329,139 B2 | 2/2008 | Benham |
| 7,333,850 B2 | 2/2008 | Marossero et al. |
| 7,335,053 B2 | 2/2008 | Avevor et al. |
| 7,347,710 B2 | 3/2008 | Ohtaka et al. |
| 7,347,826 B1 | 3/2008 | Karicherla et al. |
| 7,359,751 B1 | 4/2008 | Erickson et al. |
| 7,361,058 B1 | 4/2008 | Lien et al. |
| 7,364,440 B2 | 4/2008 | Gobron et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achter et al. |
| 7,445,512 B1 | 11/2008 | Lai |
| 7,445,522 B2 | 11/2008 | Burnes |
| 7,462,074 B1 | 12/2008 | Devlin et al. |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| D609,813 S | 2/2010 | Molden et al. |
| 7,666,028 B2 | 2/2010 | Meleck |
| D629,358 S | 12/2010 | Slippy et al. |
| 7,950,971 B2 | 5/2011 | Hobet et al. |
| 8,038,484 B2 | 10/2011 | Selvitelli et al. |
| 8,152,571 B2 | 4/2012 | Selvitelli et al. |
| 8,251,736 B2 | 8/2012 | McIntire et al. |
| 8,255,041 B2 | 8/2012 | Istvan et al. |
| D675,738 S | 2/2013 | Baumer et al. |
| 8,408,507 B2 | 4/2013 | Liu |
| 8,408,948 B2 | 4/2013 | Selvitelli et al. |
| 8,414,315 B2 | 4/2013 | Dekoski |
| D689,614 S | 9/2013 | Browne et al. |
| D699,360 S | 2/2014 | Marzynski et al. |
| 8,690,611 B2 | 4/2014 | Selvitelli et al. |
| 8,694,080 B2 | 4/2014 | Farrior |
| 8,795,004 B2 | 8/2014 | Selvitelli et al. |
| 8,897,865 B2 | 11/2014 | Farrior |
| D718,867 S | 12/2014 | Schroderus |
| 9,107,594 B2 | 8/2015 | Selvitelli et al. |
| D737,979 S | 9/2015 | Selvitelli et al. |
| 9,408,546 B2 | 8/2016 | Callahan |
| 9,408,547 B2 | 8/2016 | Zhou et al. |
| D771,818 S | 11/2016 | Callahan |
| 2001/0053639 A1 | 12/2001 | Endo |
| 2002/0133069 A1 | 9/2002 | Roberts |
| 2002/0137997 A1 | 9/2002 | Mastrototaro et al. |
| 2002/0138011 A1 | 9/2002 | Rantala |
| 2002/0188216 A1 | 12/2002 | Kayyali et al. |
| 2003/0068914 A1 | 4/2003 | Merry et al. |
| 2003/0068918 A1 | 4/2003 | Christensson |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2004/0203273 A1 | 10/2004 | Schwarz |
| 2005/0016825 A1 | 1/2005 | Endres et al. |
| 2005/0164551 A1 | 7/2005 | Wlos |

(56) References Cited

U.S. PATENT DOCUMENTS

| | | |
|---|---|---|
| 2005/0177052 A1 | 8/2005 | Istvan et al. |
| 2005/0203349 A1 | 9/2005 | Nanikashvili |
| 2006/0004273 A1 | 1/2006 | Lobodzinski |
| 2006/0073728 A1 | 4/2006 | Zaiken et al. |
| 2006/0110962 A1 | 5/2006 | Powell et al. |
| 2006/0286861 A1 | 12/2006 | Avevor et al. |
| 2007/0038057 A1 | 2/2007 | Nam et al. |
| 2007/0260133 A1 | 11/2007 | Meyer |
| 2008/0132106 A1 | 6/2008 | Burnes et al. |
| 2008/0132773 A1* | 6/2008 | Burnes ............ A61B 5/04085 600/394 |
| 2008/0177168 A1 | 7/2008 | Callahan et al. |
| 2009/0099423 A1 | 4/2009 | Al-Ali et al. |
| 2009/0149731 A1 | 6/2009 | Selvitelli et al. |
| 2009/0221153 A1 | 9/2009 | Santangelo et al. |
| 2009/0270709 A1 | 10/2009 | Copp et al. |
| 2010/0059722 A1 | 3/2010 | Copp-Howland et al. |
| 2011/0092833 A1 | 4/2011 | Farrior |
| 2011/0275252 A1 | 11/2011 | Selvitelli et al. |
| 2012/0196474 A1 | 8/2012 | Selvitelli et al. |
| 2013/0023750 A1 | 1/2013 | Callahan et al. |
| 2013/0189881 A1 | 7/2013 | Selvitelli et al. |
| 2014/0170896 A1 | 6/2014 | Selvitelli et al. |
| 2014/0180148 A1 | 6/2014 | Coggins et al. |
| 2014/0243644 A1 | 8/2014 | Farrior |
| 2014/0303472 A1 | 10/2014 | Callahan |
| 2014/0309514 A1 | 10/2014 | Zhou et al. |
| 2014/0322945 A1 | 10/2014 | Selvitelli et al. |
| 2016/0192851 A1 | 7/2016 | Selvitelli et al. |

FOREIGN PATENT DOCUMENTS

| | | |
|---|---|---|
| CN | 101491437 A | 7/2009 |
| CN | 101491438 | 7/2009 |
| CN | 102164538 A | 8/2011 |
| CN | 102185192 A | 9/2011 |
| DE | 3523226 A1 | 1/1987 |
| DE | 9002539 U1 | 5/1990 |
| DE | 10225621 | 1/2004 |
| DE | 102004032410 | 1/2006 |
| EP | 0522693 A1 | 1/1993 |
| EP | 0 766 946 A2 | 4/1997 |
| EP | 0 799 628 | 10/1997 |
| EP | 1 050 269 | 11/2000 |
| EP | 1 645 224 | 4/2008 |
| EP | 1 932 470 | 6/2008 |
| EP | 2 070474 | 6/2009 |
| EP | 2339696 A1 | 6/2011 |
| GB | 162804 | 5/1921 |
| JP | 10248820 A | 9/1998 |
| JP | 2003/010138 | 1/2003 |
| JP | 2004/282608 | 10/2004 |
| WO | WO 03 047 427 | 6/2003 |
| WO | WO 2008/092098 A2 | 7/2008 |
| WO | WO 2013/013370 A1 | 1/2013 |

OTHER PUBLICATIONS

International Preliminary Report on Patentability dated Jan. 26, 2014 for PCT Application No. PCT/CN2011/077506; 8 pages.
Office Action dated May 4, 2015 for Canadian Application No. 2,646,037; 4 pages.
Office Action dated Jul. 23, 2015 for Chinese Application No. 201180072455.9; 7 pages.
Office Action dated Aug. 17, 2015 for Canadian Application No. 2841601, 5 pages.
Response to office action filed Aug. 7, 2015 for European Application No. 14197698.5; 27 pages.
Notice of Allowance dated Aug. 26, 2015 for U.S. Appl. No. 14/160,798; 12 pages.
International Search Report and Written Opinion dated Sep. 9, 2014 for PCT Application No. PCT/US2014/027328; 16 pages.
Office Action dated Sep. 10, 2014 for U.S. Appl. No. 14/324,380; 7 pages.
Response to Examiner's Report filed Nov. 4, 2015 for Canadian Application No. 2646037; 22 pages.
Summons to Attend Oral Proceedings Pursuant to Rule 115(1) EPO dated Nov. 2, 2015 for European Application No. 08171185.5; 3 pages.
Response to Office Action filed Sep. 29, 2015 and letter from Chinese Associate for Chinese Application No. 201180072455.9, 3 pages.
International Preliminary Report of Patentability dated Oct. 26, 2015 for PCT Application No. PCT/US2014/019479, 8 pages.
Response filed on Feb. 6, 2015; for Office Action dated Sep. 10, 2014; for U.S. Appl. No. 14/324,380; 8 pages.
Chinese Office Action dated Jan. 12, 2015; with English Translation for Chinese App. No. 200180072455.9; 15 pages.
Notice of Allowance dated Mar. 30, 2015 for U.S. Appl. No. 13/987,326; 7 pages.
Notice of Allowance dated Mar. 31, 2015 for U.S. Appl. No. 14/324,380; 9 pages.
Office Action dated Apr. 10, 2015 for U.S. Appl. No. 14/160,798; 9 pages.
European Search Report dated Apr. 17, 2015 for European Application No. 14197698.5; 7 pages.
Notification to Grant dated May 25, 2015 for Chinese Application No. 201310064924.3; 5 pages.
Notice of Allowance dated Apr. 23, 2015 for European Application No. 12187209.7; 39 pages.
Communication Pursuant to Rules 70(2) and 70a(2) EPC and reference to Rule 39(1) EPC dated May 26, 2015 for European Application No. 14197698.5; 2 pages.
U.S. Appl. No. 14/041,484.
Response to Office Action filed on Oct. 23, 2014 for U.S. Appl. No. 13/987,326; 8 pages.
Office Action dated Aug. 6, 2014 for Chinese Application No. 201010624971.5; 17 pages.
Office Action dated Jun. 28, 2014 for Australian Application No. 2010235901, 4 pages.
Response to office Action filed Jun. 1, 2015 for European Application No. 11869957.8; 10 pages.
Response to Office Action with English translation filed Feb. 2, 2015 for Chinese Application No. 201310064924.3; 23 pages.
Response to Office Action with English translation filed May 27, 2015 for Chinese Application No. 201180072455.9; 15 pages.
Ex Parte Quayle Action dated Aug. 14, 2015 corresponding to U.S. Appl. No. 29/498,717; 38 Pages.
Response to Chinese Office Action filed Oct. 24, 2014 with English translation for Chinese Application No. 201310064924.3; 27 pages.
Letter from CCPIT Patent and Trademark Law Office dated Jan. 2, 2015 for Chinese Application No. 201310064924.3, 7 pages.
Chinese Office Action dated Nov. 17, 2014 for Chinese Application No. 201310064924.3, 3 pages.
European Extended Search Report dated Nov. 18, 2014 for European Application No. 11869957.8; 9 pages.
Response to Office Action filed Oct. 24, 2014 for U.S. Appl. No. 13/987,326; 8 pages.
Notice of Allowance dated Nov. 18, 2014 for U.S. Appl. No. 13/987,326; 4 pages.
U.S. Appl. No. 13/785,713, filed Mar. 5, 2013, 200 pages, Part 5.
U.S. Appl. No. 13/785,713, filed Mar. 5, 2013, 200 pages, Part 6.
U.S. Appl. No. 13/785,713, filed Mar. 5, 2013, 200 pages, Part 7.
U.S. Appl. No. 13/785,713, filed Mar. 5, 2013, 200 pages, Part 8.
U.S. Appl. No. 13/785,713, filed Mar. 5, 2013, 200 pages, Part 9.
U.S. Appl. No. 13/785,713, filed Mar. 5, 2013, 200 pages, Part 10.
U.S. Appl. No. 13/785,713, filed Mar. 5, 2013, 200 pages, Part 11.
U.S. Appl. No. 13/785,713, filed Mar. 5, 2013, 200 pages, Part 12.
U.S. Appl. No. 13/785,713, filed Mar. 5, 2013, 200 pages, Part 13.
U.S. Appl. No. 13/785,713, filed Mar. 5, 2013, 18 pages, Part 14.
U.S. Appl. No. 14/041,471; Part 1 of 16; 350 Pages.
U.S. Appl. No. 14/041,471; Part 2 of 16; 350 Pages.
U.S. Appl. No. 14/041,471; Part 3 of 16; 350 Pages.
U.S. Appl. No. 14/041,471; Part 4 of 16; 350 Pages.
U.S. Appl. No. 14/041,471; Part 5 of 16; 350 Pages.

(56) References Cited

OTHER PUBLICATIONS

U.S. Appl. No. 14/041,471; Part 6 of 16; 350 Pages.
U.S. Appl. No. 14/041,471; Part 7 of 16; 350 Pages.
U.S. Appl. No. 14/041,471; Part 8 of 16; 350 Pages.
U.S. Appl. No. 14/041,471; Part 9 of 16; 150 Pages.
Notice of Allowance dated Oct. 29, 2015 for U.S. Appl. No. 13/987,326; 6 pages.
Notice of Allowance dated Dec. 24, 2015 for U.S. Appl. No. 14/160,798; 6 pages.
Response to Examiner's Report filed Nov. 30, 2015 for Canadian Application No. 2,841,601; 11 pages.
Notice of Allowance dated Jun. 25, 2015 for U.S. Appl. No. 14/324,380; 5 pages.
Response to Office Action filed Jul. 8, 2015 U.S. Appl. No. 14/160,798; 8 pages.
Notice of Allowance dated Jul. 17, 2015 for U.S. Appl. No. 13/987,326; 7 pages.
A&D Company, Limited, "Vital Sensor Graphic Model", No. TM-2560G/TM2564-G-TM-2564GP/TM2564GP, Jan. 1, 2004; pp. 1-62.
Andreas Boos et al.; "A New Lightweight Fetal Telemetry System", Dec. 1995; Hewlett-Packard Journal; 12 pages.
Tyco Healthcare Kendal ECG Electrodes Where Quality leads 2003 8 pages.
Europeanm Search Report Corresponding to European Application No. EP 07 25 3850, Date of completion is Dec. 21, 2007 3 pages.
EP Notice Under Rule 161 dated Feb. 28, 2014, for EP App. No. 11869957.8 3 pages.
Response to Written Opinion and Claims Filed on Jun. 11, 2014, for EP Appl. No. 11869957.8 6 pages.
Search Report and Written Opinion dated Apr. 12, 2012, for App. No. PCT/CN2011/077506 14 pages.
First Office Action dated Jul. 26, 2011, for Chinese App. No. 200810191090.1 6 pages.
Letter regarding Response to Office Action dated Nov. 22, 2011, for Chinese App. No. 200810191090.1 9 pages.
Response to Office Action dated Dec. 12, 2011, for Chinese App. No. 200810191090.1 18 pages.
Letter dated May 11, 2012 enclosing Second Office Action dated Apr. 27, 2012, for Chinese App. No. 200810191090.1 6 pages.
Notification of Response to Second Office Action dated Jun. 11, 2012, for Chinese App. No. 200810191090.1 5 pages.
Letter dated Dec. 20, 2012 enclosing Grant Notification dated Dec. 19, 2012, for Chinese App. No. 200810191090.1 4 pages.
Divisional Application as filed on Mar. 1, 2013, for Chinese App. No. 200810191090.1 37 pages.
European Office Action dated Nov. 19, 2010, for EP App. No. 08171185.5 1 page.
Letter dated Dec. 22, 2010 in response to EP Office Action Nov. 19, 2010 European Office Action for EP App. No. 08171185.5 1 page.
Response to Office Action dated Oct. 3, 2012 for EP App. No. 08171185.5 2 page.
Letter dated Oct. 4, 2012 and Divisional for EP App. No. 08171185.5 39 pages.
Letter dated Dec. 16, 2013 In response to Commumication dated Jun. 24, 2013, for EP App. No. 08171185.5 4 pages.
Examination Report dated Jun. 24, 2013, for EP App. No. 08171185.5 4 pages.
Extended Search Report dated Mar. 7, 2012, for EP App. No. 08171185.5 8 pages.
Letter dated Apr. 2, 2012 and Office Action for Mexican App. No. MX/a/2008/015927 3 pages.
Letter dated May 15, 2012 and Response to Office Action for Mexican App. No. MX/a/2008/015927 Filed on Dec. 11, 2008 9 Pages.
Letter dated Jun. 26, 2012 and Regarding Notice of Allowance with allowed claims for Mexican App. No. MX/a/2008/015927 Filed on Dec. 11, 2008 7 Pages.
Letter dated Feb. 5, 2014 Confirming receipt of Notice of Allowance, for Mexican App. No. MX/a/2012/009542 2 pages.

Letter dated Feb. 25, 2013 also enclosing Office Action for App. No. MX/a/2012/009542 3 pages.
Letter and Response to Office Action dated Apr. 23, 2013, for Mexican App. No. MX/a/2012/009542 20 pages.
Letter dated Sep. 18, 2013 and Office Action for Mexican App. No. MX/a/2012/009542 4 pages.
Letter dated Oct. 30, 2013 and Response to Office Action for Mexican App. No. MX/a/2012/009542 5 pages.
Letter dated Jun. 10, 2014 Confirming receipt of Notice of Allowance for Mexican App. No. MX/a/2013/012636 2 pages.
Letter dated Jun. 10, 2014 Confirming receipt of Notice of Allowance for Mexican App. No. MX/a/2013/012635 2 pages.
Extended Search Report dated Oct. 8, 2013, for EP App. No. 12187209.7009542 6 pages.
European Notice Responding to Search Report dated Nov. 11, 2013, for EP App. No. 12187209.7009542 2 pages.
European Exam Report dated Mar. 11, 2014, for EP App. No. 12187209.7009542 4 pages.
Response dated Jan. 27, 2014 to Extended Search Report dated Oct. 8, 2013, for EP App. No. 12187209.7009542 16 pages.
Response to Exam Report dated Jun. 24, 2014 for EP App. No. 12187209.7009542 8 pages.
Response dated Nov. 2, 2011 to Communication dated May 10, 2011 for EP App. No. 10013624.10 5 pages.
Extended Search Report dated Apr. 4, 2011, for EP App. No. 10013624.10 14 pages.
European Exam Report dated Nov. 12, 2013, for EP App. No. 12187209.7009542 6 pages.
Response to Communication dated Mar. 17, 2014 for EP App. No. 12187209.7009542 14 pages.
European Office Action dated May 21, 2014, for EP App. No. 12187209.7009542 5 pages.
European Search Report dated May 23, 2014, for EP App. No. 14162076.5 10 pages.
Response to Chinese Office Action dated May 4, 2011, for Chinese App. No. 201010624971.50 21 pages.
Notification of Entry into Examination Procedure dated Oct. 11, 2012, for Chinese App. No. 201010624971.50 2 Pages.
Receipt of First Office Action dated Nov. 28, 2013, for Chinese App. No. 201010624971.50 136 Pages.
Response to Office Action dated Apr. 14, 2014, for Chinese App. No. 20101624971.50 34 Pages.
Search Report dated Jun. 4, 2014, for App. No. PCT/US2014/019479 10 pages.
Atlicle 19 Amendment as filed dated Jul. 2, 2014 for App. No. PCT/US2014/019479 10 pages.
Letter and Chinese Office Action dated Jul. 1, 2014, for Chinese App. No. 2013100649128.3 38 pages.
Voluntary Amendment with English claims dated Jul. 15, 2014 for Application No. 201180072455.9 7 pages.
Preliminary Amendment dated Jul. 7, 2014 for U.S. Appl. No. 14/324,380 6 pages.
Partial Search Report dated Jun. 5, 2014 for Application No. PCT/US2014/027328 6 pages.
Callahan U.S. Appl. No. 13/987,326, filed Mar. 15, 2013 37 pages.
Zhou U.S. Appl. No. 14/160,798, filed Jan. 22, 2014 26 pages.
Selvitelli U.S. Appl. No. 14/324,380, filed Jul. 7, 2014 41 pages.
U.S. Appl. No. 12/330,550; 175 Pages.
U.S. Appl. No. 13/182,656; 143 Pages.
U.S. Appl. No. 13/443,096; 50 Pages.
U.S. Appl. No. 13/785,713, filed Mar. 5, 2013, 200pages, Part 1.
U.S. Appl. No. 13/785,713, filed Mar. 5, 2013, 200 pages, Part 2.
U.S. Appl. No. 13/785,713, filed Mar. 5, 2013, 200 pages, Part 3.
U.S. Appl. No. 13/785,713, filed Mar. 5, 2013, 200 pages, Part 4.
U.S. Appl. No. 14/041,471; Part 9A of 16; 200 Pages.
U.S. Appl. No. 14/041,471; Part 10 of 16; 350 Pages.
U.S. Appl. No. 14/041,471; Part 11 of 16; 350 Pages.
U.S. Appl. No. 14/041,471; Part 12 of 16; 350 Pages.
U.S. Appl. No. 14/041,471; Part 13 of 16; 350 Pages.
U.S. Appl. No. 14/041,471; Part 14 of 16; 350 Pages.
U.S. Appl. No. 14/041,471; Part 15 of 16; 350 Pages.
U.S. Appl. No. 14/041,471; Part 16 of 16; 138 Pages.
U.S. Appl. No. 12/876,316; Part 1 of 5; 250 Pages.

(56) References Cited

OTHER PUBLICATIONS

U.S. Appl. No. 12/876,316; Part 2 of 5; 250 Pages.
U.S. Appl. No. 12/876,316; Part 3 of 5; 250 Pages.
U.S. Appl. No. 12/876,316; Part 4 of 5; 250 Pages.
U.S. Appl. No. 12/876,316; Part 5 of 5; 238 Pages.
U.S. Appl. No. 14/195,140; 314 Pages.
U.S. Appl. No. 61/793,284; 50 Pages.
U.S. Appl. No. 13/987,326; 90 Pages.
Decision to Grant dated Nov. 5, 2015 for Chinese Patent Application No. 201180072455.9; 6 pages.
Notice of Allowance from U.S. Appl. No. 29/498,717, mailed Jul. 19, 2016, 8 pp.
Notice of Allowance from U.S. Appl. No. 14/825,206, mailed Jul. 27, 2016, 8 pp.
Prosecution History from U.S. Appl. No. 13/987,326, dated Jun. 9, 2014 through Jun. 22, 2016, 58 pp.
U.S. Appl. No. 29/528,574, by David Selvitelli, filed May, 29, 2015.
PCT International Preliminary Report on Patentability and Written Opinion of the ISA dated Sep. 15, 2015 for PCT App. No. PCT/US2014/019479; 7 pages.
Prosecution History from U.S. Appl. No. 14/160,798, dated Apr. 10, 2015 through Apr. 8, 2016, 44 pp.
Prosecution History from U.S. Appl. No. 14/041,484, dated Sep. 30, 2013 through Mar. 27, 2014, 23 pp.
Prosecution History from U.S. Appl. No. 29/498,717, dated Aug. 14, 2015 through May 24, 2016, 41 pp.
Prosecution History from U.S. Appl. No. 14/324,380, dated Jul. 7, 2014 through Jun. 25, 2015, 57 pp.
Prosecution History from U.S. Appl. No. 13/785,713, dated Mar. 5, 2013 through Feb. 14, 2014, 39 pp.
Prosecution History from U.S. Appl. No. 14/825,206, dated Mar. 17, 2016 through Jul. 27, 2016, 24 pp.
Prosecution History from U.S. Appl. No. 12/330,550, dated Nov. 30, 2010 through Jul. 8, 2011, 35 pp.
Prosecution History from U.S. Appl. No. 13/182,656, dated Jul. 14, 2011 through Dec. 5, 2011, 32 pp.
Prosecution History from U.S. Appl. No. 13/443,096, dated Apr. 10, 2012 through Feb. 13, 2013, 44 pp.
Prosecution History from U.S. Appl. No. 12/876,316, dated Jul. 20, 2012 through May 28, 2013, 74 pp.
Prosecution History from U.S. Appl. No. 14/041,471, dated Sep. 30, 2013 through May 23, 2014, 44 pp.
Prosecution History from U.S. Appl. No. 14/195,140, dated May 19, 2014 through Jul. 25, 2014, 87 pp.
Prosecution History from U.S. Appl. No. 29/486,095, dated Jul. 15, 2014 through May 15, 2015, 57 pp.
Prosecution History from U.S. Appl. No. 15/230,935, dated Aug. 9, 2016 through Jan. 23, 2017, 24 pp.
First Office Action and Search Report, and translation thereof, from counterpart Chinese Application No. 201480021628.8, dated Oct. 17, 2016, 13 pp.
Office Action from U.S. Appl. No. 15/230,935, dated Oct. 20, 2016, 10 pp.
Notice of Allowance from U.S. Appl. No. 29/528,574, mailed Jan. 25, 2017, 8 pp.
International Preliminary Report on Patentability for PCT Application No. PCT/US2014/027328; 12 pages.
Office Action from U.S. Appl. No. 15/218,339, dated Mar. 16, 2017, 10 pp.
Notice of Allowance from U.S. Appl. No. 15/230,935, mailed Apr. 21, 2017, 6 pp.

\* cited by examiner

ELECTRODE CONNECTOR DESIGN TO AID IN CORRECT PLACEMENT

CROSS REFERENCE TO RELATED APPLICATIONS

This application claims priority under 35 U.S.C. §119 to U.S. Provisional application Ser. No. 61/793,284 entitled ELECTRODE CONNECTOR WITH A CONDUCTIVE MEMBER filed on Mar. 15, 2013 which is incorporated herein by reference for all purposes.

BACKGROUND

Technical Field

The present disclosure relates to an electrocardiograph system, and more particularly, to an electrode connector including an electrically conductive member for facilitating positioning of an electrode on a patient.

Background of Related Art

Electrocardiograph (ECG) systems are widely used to obtain biopotential signals containing information indicative of the electrical activity associated with the heart and pulmonary system. To obtain biopotential signals ECG electrodes are applied to the skin of a patient in various locations and coupled to an ECG device, e.g., an "ECG monitor" or "ECG telemetry." Placement of the electrodes is dependant on the information sought by the clinician.

The placement of the ECG electrodes on the patient has been established by medical protocols. The most common protocols require the placement of the electrodes in a 3-lead, a 5-lead or a 12-lead configuration. A 3-lead configuration requires the placement of three electrodes; one electrode adjacent each clavicle bone on the upper chest and a third electrode adjacent the patient's lower left abdomen. A 5-lead configuration requires the placement of the three electrodes in the 3-lead configuration with the addition of a fourth electrode adjacent the sternum and a fifth electrode on the patient's lower right abdomen. A 12-lead configuration requires the placement of 10 electrodes on the patient's body. Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III).

After placement of electrodes on the patient, the electrodes connect to an ECG device by an ECG lead set. One end of the ECG lead set, closest to the patient, connects to each electrode (alternatively, the electrodes may be integrated into the distal end of the ECG lead set) and receives biopotential signals from the body. The other end of the ECG lead set connects to the ECG input connector and supplies the biopotential signals received from the body to the ECG device.

To achieve proper results, the clinician, must be careful to place each electrode at its precise location on the patient. When using individual electrodes, this procedure can prove to be inconvenient, time consuming, and inaccurate. Accordingly, a need exists for an electrode connector that can aid precise placement of the electrode on the patient.

SUMMARY

In accordance with an embodiment of the present disclosure, there is provided an electrode connector including a housing, an electrically conductive contact plate, a lead wire terminal electrically connected to the contact plate and an electrically conductive member. The housing defines a first opening configured to receive at least a portion of an electrode therethrough. The electrically conductive contact plate defines a bore aligned with the first opening. The bore is configured and dimensioned to receive at least a portion of the electrode therein. The electrically conductive member is electrically coupled to the lead wire terminal. The electrically conductive member is supported on the housing and is spaced apart from the first opening.

In an embodiment, the electrically conductive member may have a hemispherical shape. In addition, the electrically conductive member may be hingedly supported within the housing. The electrically conductive member may include a biasing member to bias the electrically conductive member away from the housing.

In another embodiment, the housing may define a chamber configured and dimensioned to receive the electrically conductive member therein. The chamber may include an opening through which the electrically conductive member extends. In addition, the chamber may include a slidable member movable between open and closed positions to open and close the opening of the chamber. The slidable member may be made of an electrically insulative material.

In yet another embodiment, the electrically conductive member may be made of plastic and may include a conductive filler. Alternatively, the electrically conductive member may be made of conductive polymers. The electrically conductive member may be disposed in a second opening defined in the housing. The first and second openings may be defined in opposing sides of the housing. In addition, the electrically conductive member may protrude from the housing.

In still yet another embodiment, the electrode connector may further include a lever pivotally coupled to the housing. The lever may be pivotable between a first position in which at least a portion of the lever extends across the bore of the contact plate to secure at least a portion of the electrode therein and a second position in which the lever is positioned such that the bore is unobstructed. In addition, the lever may further include a biasing member to bias the lever toward the first position. The lever may further include a finger configured and adapted to engage the electrode to secure the electrode within the bore of the contact plate when the lever is in the first position.

In accordance with another aspect of the present disclosure, there is provided a method of monitoring ECG data. The method includes the steps of providing an electrode connector including an electrically conductive contact plate defining a bore configured and dimensioned to receive at least a portion of an electrode therein, a lead wire terminal electrically connected to the contact plate, and an electrically conductive member electrically coupled to the lead wire terminal. The method further includes electrically connecting the electrode connector to an ECG monitoring system to be used, contacting the electrically conductive member of the electrode connector against a patient, moving the electrode connector, while the electrically conductive member is in contact with the patient, to a location on the patient providing a strong trace signal on the ECG system, and placing an electrode on the patient at the location providing the strong trace signal.

In an embodiment, the method may further include the step of connecting the electrode connector to the electrode.

In addition, the method may also include the step of measuring biopotential signals from the electrode with the ECG system.

In another embodiment, the electrode connector may define a chamber configured and dimensioned to receive the electrically conductive member therein. The electrically conductive member may be movable between a retracted position in which the electrically conductive member is disposed within the chamber and an extended position in which the member at least partially extends out of the chamber. The method may further include the step of placing the electrically conductive member in the retracted position prior to placing an electrode on the patient.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
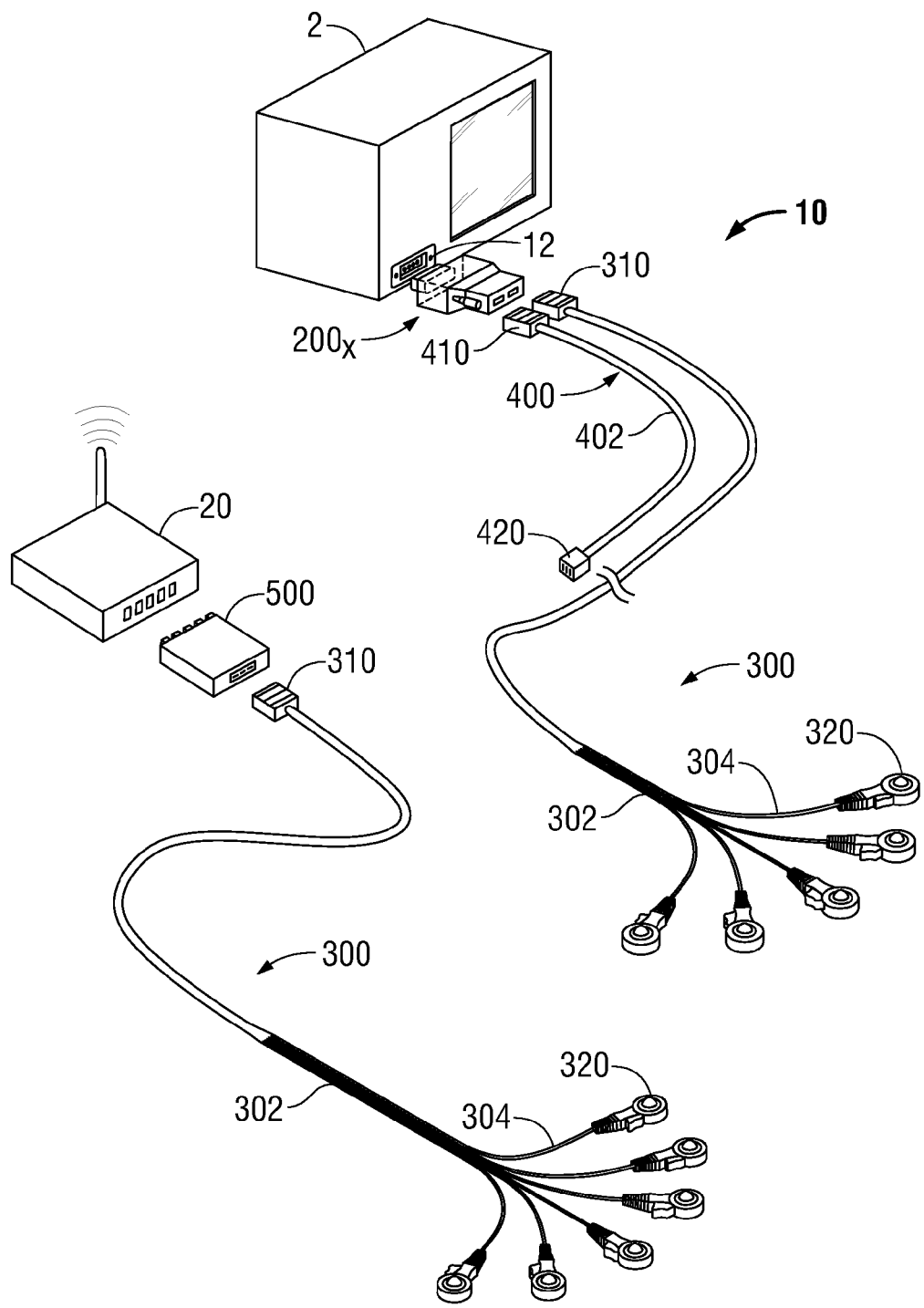
FIG. 1 is a schematic illustration of an ECG system including electrode connectors in accordance with an embodiment of the present disclosure.

Embodiments of the present disclosure will now be described in detail with reference to the drawings, in which like reference numerals designate identical or corresponding elements in each of the several views. As used herein and as is traditional, the term "distal" refers to the portion which is farthest from the user/clinician, and the term "proximal" refers to the portion that is closest to the user/clinician. In addition, terms such as "above", "below", "forward", "rearward", etc. refer to the orientation of the figures or the direction of components and are simply used for convenience of description. As used herein, the term "patient" should be understood as referring to a human subject or other animal, and the term "clinician" should be understood as referring to a doctor, nurse, or other care provider and may include support personnel. "Radiotransparency" may be used interchangeably with "radiolucency", and refers to the property of an electrode that allows a clinician to leave electrodes in place during radiological (e.g., x-ray) or other imaging examinations, to visualize tissue underlying the electrode without loss of image quality. In the following description, well-known functions or constructions are not described in detail to avoid obscuring the present disclosure in unnecessary detail.

Various exemplary embodiments of the present disclosure are discussed hereinbelow in terms of ECG electrodes for monitoring heart activity and for diagnosing heart abnormalities. It is envisioned, however, that the principles of the present disclosure are equally applicable to other biomedical electrodes, for example, electroencephalogram (EEG) electrodes; transcutaneous electrical nerve stimulation (TENS) electrodes used for pain management; neuromuscular stimulation (NMS) electrodes used for treating conditions such as scoliosis; muscle stimulation electrodes; wound treatment electrodes (accelerating healing of skin wounds or broken bones); defibrillation electrodes to dispense electrical energy to a chest cavity of a patient to defibrillate heart beats of the patient; iontophoresis; and dispersive electrodes to receive electrical energy dispensed into an incision made during electrosurgery.

Figure 2:
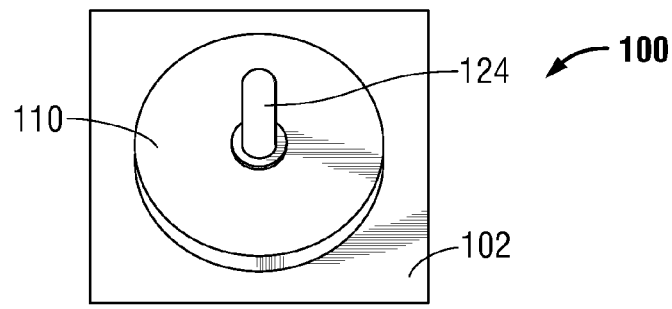
FIG. 2 is a perspective view of a biomedical electrode for use with the ECG system of FIG. 1.

With reference to FIG. 1, an electrocardiograph (ECG) system for obtaining biopotential signals containing information indicative of the electrical activity associated with the heart and pulmonary system is shown generally as 10. ECG system 10 includes an ECG device, in the form of an ECG floor monitor 2 or ECG telemetry monitor 20, an ECG lead set assembly 300, and a plurality of biomedical electrodes 100 (FIG. 2). Each electrode 100 is connected to an associated one of a plurality of lead wires 304 of ECG lead set assembly 300 via a plurality of connectors 320 in accordance with an embodiment of the present disclosure. ECG floor monitor 2 monitors physiological heart potentials of a patient via electrical signals detected by electrodes 100 and/or connectors 320 and generates a trace. The trace may be displayed, recorded, analyzed or otherwise evaluated by ECG floor monitor 2, providing a diagnostic tool for detecting heart disease or defects.

In particular, ECG floor monitor 2 includes at least one lead set input connector 12 configured to connect with at least one ECG lead set assembly 300. However, lead set assembly 300 is not configured for direct connection (mechanically and/or physically incompatible) to the lead set input connector 12 of ECG floor monitor 2 or ECG telemetry monitor 20. ECG system 10 may further include an adapter $200_X$, depending on (1) the type of ECG floor monitor 2 or ECG telemetry monitor 20 present, (2) on whether a 3-lead, a 5-lead or a 12-lead electrode set assembly 300 is used, and (3) on whether one or more ECG lead set assemblies 300 are used. Device connector 310 of ECG lead set assembly 300 is coupled to the proximal end of lead set cable 302 and is configured to be coupled with lead set adapters $200_X$. Electrode connector 320 is coupled to a distal end of lead set cable 302.

Figure 3:
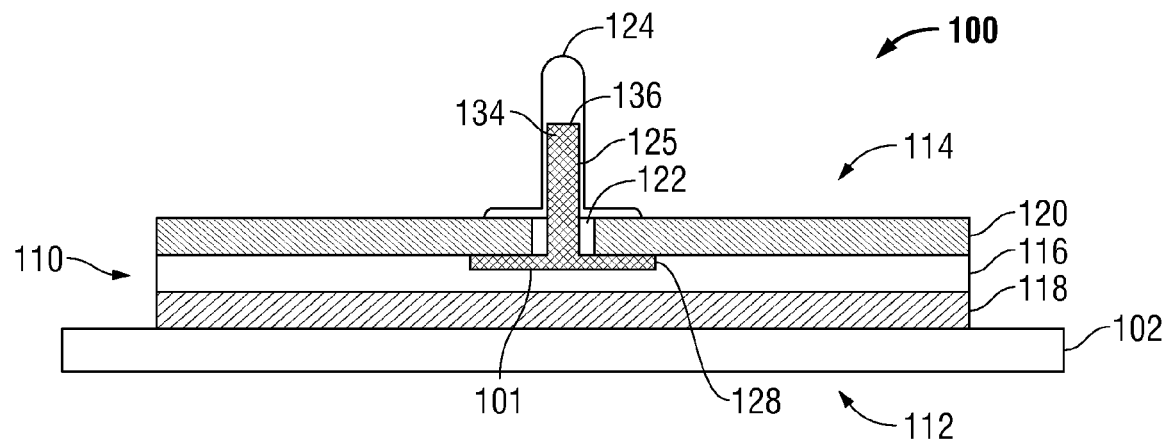
FIG. 3 is a side, cross-sectional view of the biomedical electrode of FIG. 2.

With brief reference now to FIGS. 2 and 3, a biomedical electrode 100 includes an electrode element 101, a press stud 124 adapted for mechanical and electrical coupling with lead wire 304 (FIG. 1) and a pad 110 including a patient contact side 112 and a connector side 114. Patient contact side 112 of pad 110 may include a conductive layer 116, a conductive composition 118 for application to a body surface of a patient, e.g., a skin surface, for transmitting electrical signals and/or currents to and/or from the patient, and a release liner

102. Connector side 114 of pad 110 includes a non-conductive backing layer 120 defining a central opening 122 covered by press stud 124 adapted for mechanical and electrical coupling with lead wire 304. Conductive composition 118 may be a conventional conductive gel. Other conductive compositions which may be utilized with electrode 100 of the present disclosure includes hydrogels, such as, for example, those disclosed in commonly assigned U.S. Patent Application Publication Nos. 2009/0270709, entitled "Novel Electrodes", and 2010/0059722, entitled "Conductive Compositions and Method", the entire disclosures of each of which are hereby incorporated by reference herein.

With continued reference to FIG. 3, electrode element 101 includes a base or flange portion 128 disposed between backing layer 120 and conductive layer 116 and a post 134 extending in transverse relation to base portion 128. Electrode element 101 interconnects pad 110 with press stud 124. A proximal end 136 of post 134 is secured within a channel 125 defined in press stud 124 by, for example, friction fit, or other conventional mechanical means.

With continued reference to FIG. 3, release liner 102 is a peelable or strippable protective cover member. Release liner 102 is releasably adhered to conductive composition 118 so as to form a protective covering of conductive composition 118 prior to use. Upon determining a desired position of electrode 100 on the patient, release liner 102 is peeled and removed, and electrode 100 is affixed to the desired position.

Figure 6:
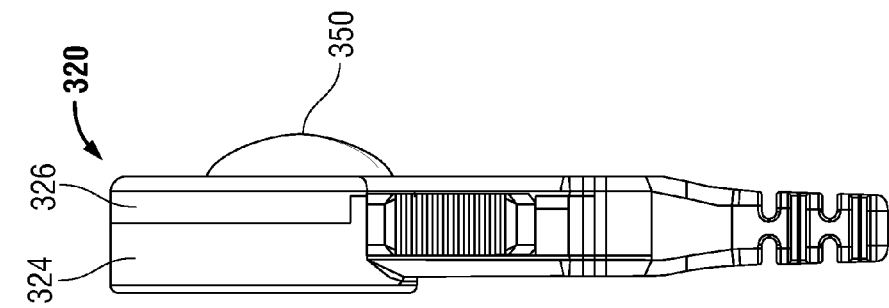
FIG. 6 is a side view of the electrode connector of FIG. 1.
Figure 5:
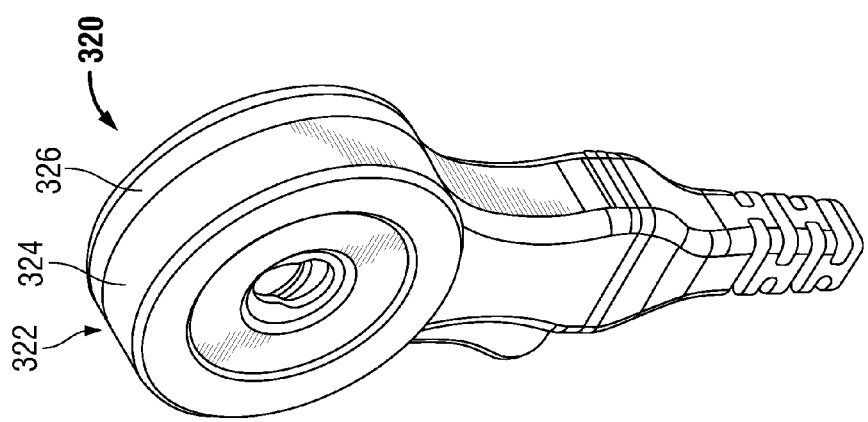
FIG. 5 is a bottom, perspective view of the electrode connector of FIG. 1.
Figure 4:
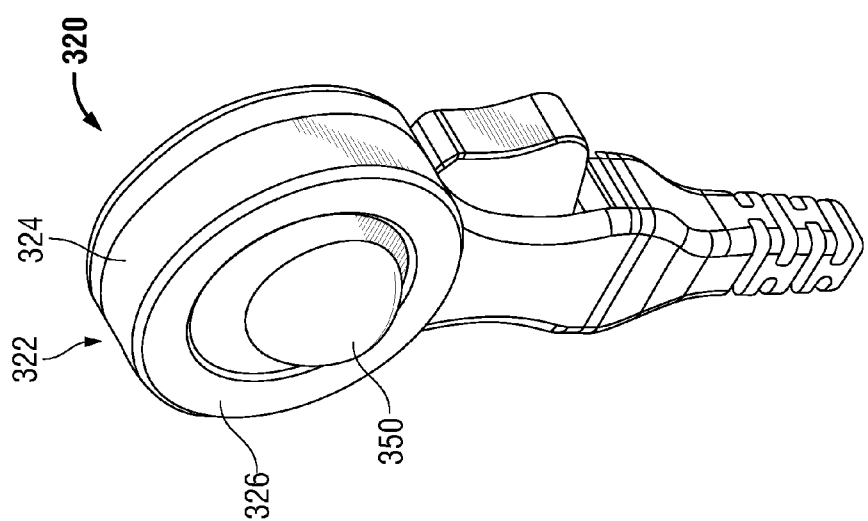
FIG. 4 is a top, perspective view of the electrode connector of FIG. 1.

With reference now to FIGS. 4-6, connector 320 in accordance with an embodiment of the present disclosure is configured to detachably connect to electrode 100 positioned on the patient to detect biopotential signals. Electrode connector 320 includes an electrically conductive member 350, in the form of, for example, a protrusion, a flat plate, or a lead wire, that enables the clinician to selectively detect biopotential signals of the patient with or without electrode 100 attached thereto. In particular, electrically conductive member 350 is disposed on one side of electrode connector 320 and another side of electrode connector 320 is configured to detachably connect to electrode 100. Under such a configuration, the clinician may utilize electrically conductive member 350 to help or facilitate placement of electrode 100 on the patient. The electrically conductive characteristic of member 350 enables the clinician to adjustably position connector 320 on the patient with or without electrode 100 attached to connector 320. Specifically, the clinician may utilize member 350 to determine a position on the patient that provides the strongest signal on ECG floor monitor 2, prior to removing release liner 102 from contact side 112 of pad 110 and affixing electrode 100 to the patient, and thereby improving the accuracy and quality of the trace.

Figure 7:
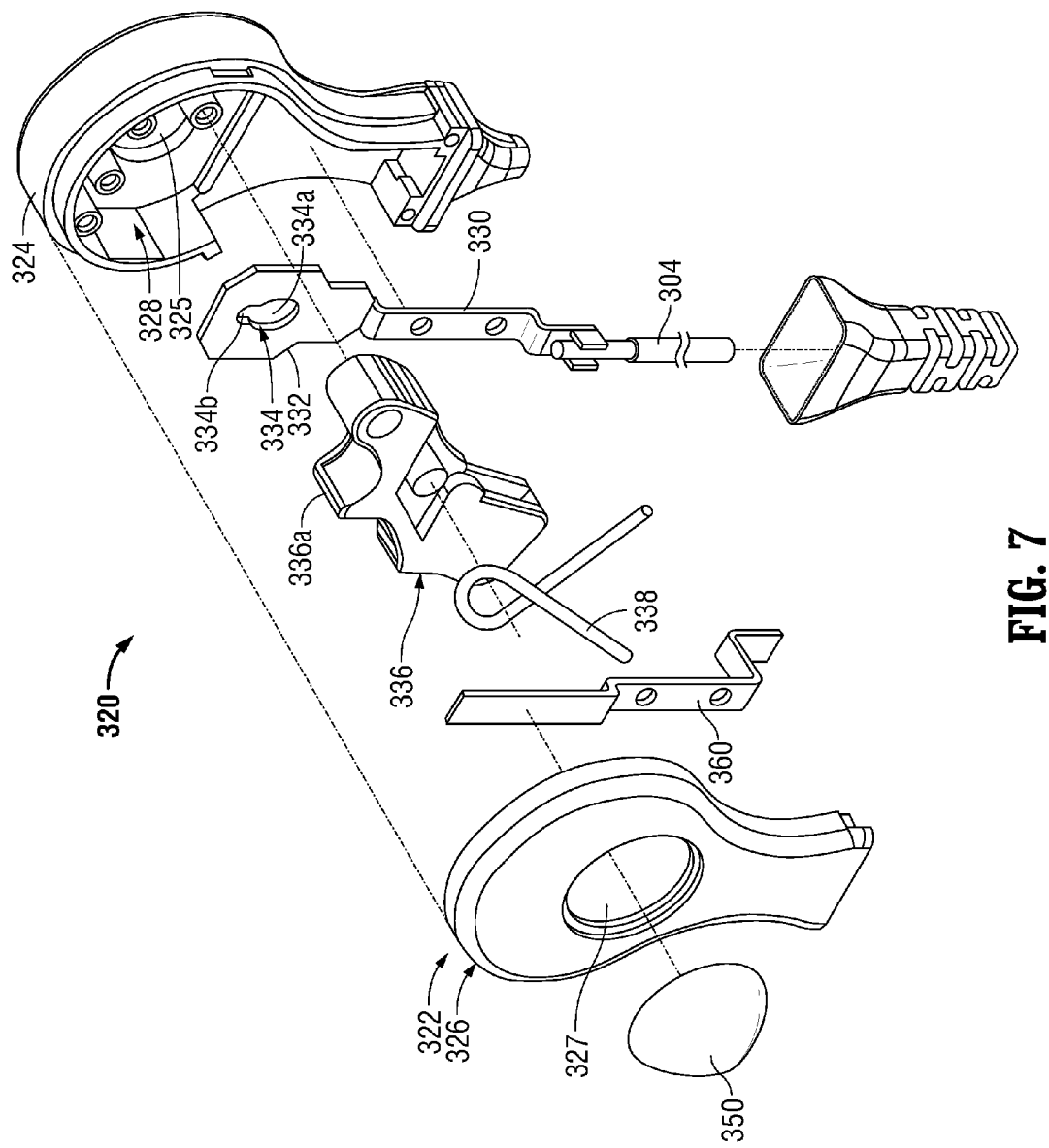
FIG. 7 is an exploded, perspective view of the electrode connector of FIG. 1 with parts separated.

With reference now to FIG. 7, electrode connector 320 includes a housing 322 having a lower member 324 and an upper member 326, and defining an internal cavity 328 therebetween. Housing 322 is fabricated from a non-conducting material, e.g., an injection molded polymer which electrically insulates the subject from the conductive element(s) therewithin. Upper member 326 and lower member 324 are separate components attached to each other by conventional means and form a non-conductive element of housing 322. Upper member 326 defines an opening 327 dimensioned to receive electrically conductive member 350 therethrough. Lower member 324 defines an opening 325 configured and dimensioned to receive at least a portion of press stud 124 of electrode 100.

With continued reference to FIG. 7, electrode connector 320 includes first and second lead wire terminals 330, 360 which are electrically connected to an end of lead wire 304. In particular, first lead wire terminal 330 is configured to be electrically coupled to electrode 100, and second lead wire terminal 360 is electrically connected to electrically conductive member 350. Housing 322 supports a contact plate 332 that is electrically connected to lead wire terminal 330. Contact plate 332 defines a keyhole slot 334 formed therein and in communication with opening 325 defined in lower member 324. Keyhole slot 334 includes first slot portion 334a and second slot portion 334b. First slot portion 334a defines an internal dimension or diameter that is greater than the corresponding internal dimension or diameter of second slot portion 334b.

Figure 8:
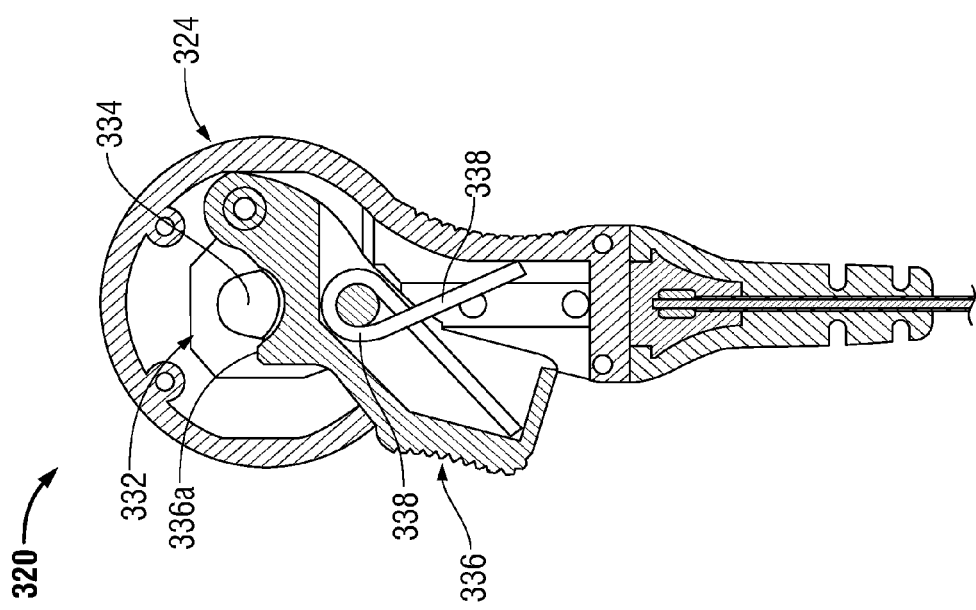
FIG. 8 is a cross-sectional view of the electrode connector of FIG. 1 illustrating a bottom half of the electrode connector.
Figure 10:
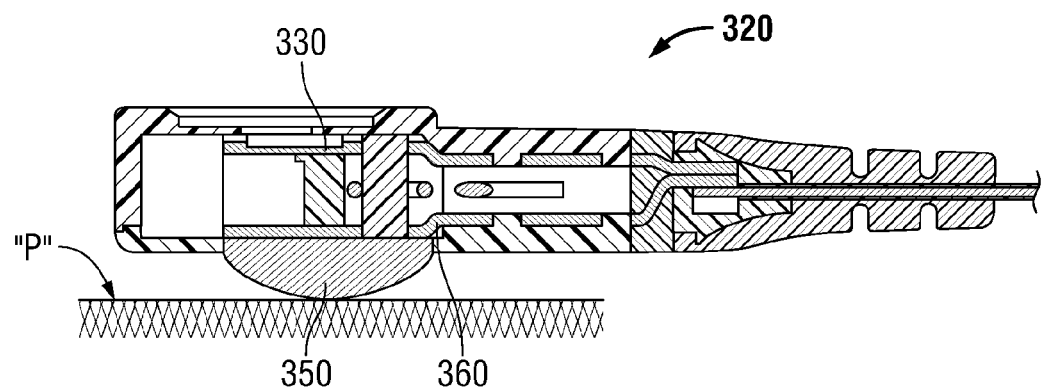
FIGS. 10 and 11 are side, cross-sectional views of the electrode connector of FIG. 1 illustrating use thereof.
Figure 11:
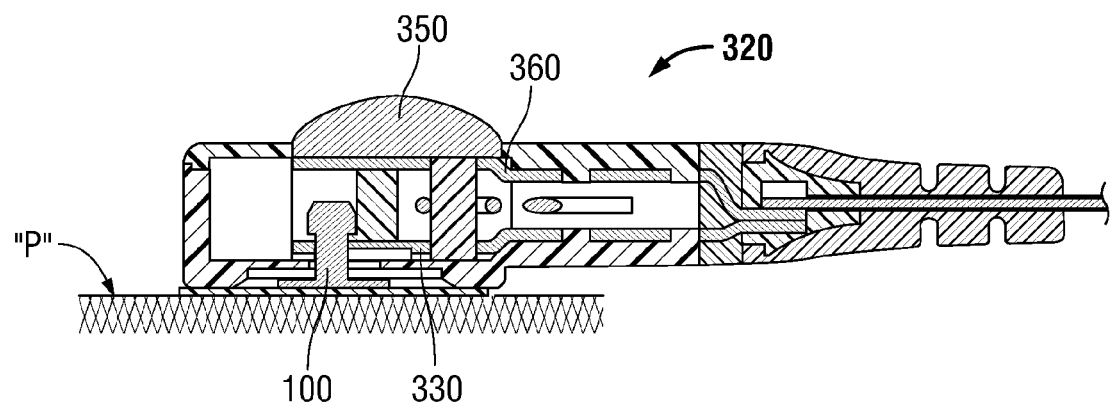

With reference now to FIGS. 7 and 8, housing 322 further includes a lever 336 pivotably connected thereto. Lever 336 is disposed between first and second lead wire terminals 330, 360. Lever 336 is biased to a first position by a biasing member 338. Lever 336 includes a cam finger 336a projecting therefrom so as to extend across first slot portion 334a of keyhole slot 334 when lever 336 is in the first position. Lever 336 is actuatable to a second position wherein cam finger 336a thereof does not obstruct or extend across first slot portion 334a of keyhole slot 334. In this manner, lever 336 of electrode connector 320 may be actuated to the second position to enable insertion of press stud 124 of electrode 100 into first slot portion 334a of keyhole slot 334. Thereafter, lever 336 may be released so that biasing member 338 moves cam finger 336a of lever 336 against press stud 124 to push or force the lower portion press stud 124 into second slot portion 334b of keyhole slot 334. The biasing force of biasing member 338 helps to maintain press stud 124 within second slot portion 334b of keyhole slot 334, and thus inhibits removal or disconnection of biomedical electrode from connector 320.

Figure 9:
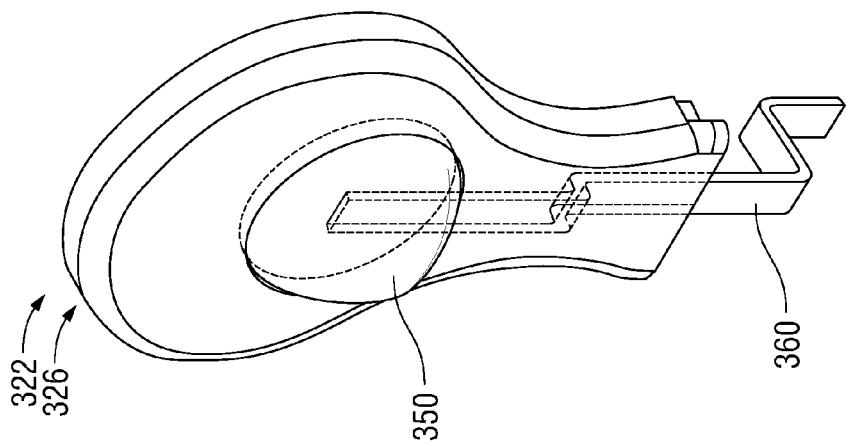
FIG. 9 is a partial, perspective view of the electrode connector of FIG. 1 illustrating a top half of the electrode connector.

With reference now to FIGS. 7 and 9, member 350 is attached to second lead wire terminal 360. In particular, member 350 and second lead wire terminal 360 are electrically conductive and are electrically coupled. Member 350 has a hemispherical shape and a smooth surface to facilitate sliding of member 350 on the surface of the patient's skin. Member 350 may be fabricated of any suitable material. Member 350 may be fabricated from plastic and include a conductive filler material to enhance the flow of energy therethrough. Fillers include, for example, conductive metal fibers such as silver or tin fibers, and metallic threads, metallic powders, metallic flakes, and metallic spheres. The filler material may be carbon fillers, conductive carbon fiber fillers, acetylene black, chopped polyacrylonitrile fibers, noble metallic particles, noble metal halide particles, and combinations thereof.

Non-limiting examples of suitable plastic materials from which member 350 may be fabricated include polyolefins, such as polyethylene and polypropylene, including atactic, isotactic, syndiotactic, and blends and combinations thereof; polyethylene glycols; polyethylene oxides; ultra high molecular weight polyethylene; copolymers of polyethylene and polypropylene, as well as polyisobutylene and ethylene-alpha olefin copolymers; fluorinated polyolefins such as polytetrafluoroethylene and polyfluroroacetal; polyamides such as nylon and polycaprolactam; polyamines; polyimines; polyesters such as polyethylene terephthalate and polybutylene terephthalate; aliphatic polyesters; polyethers such as polyether ether ketone and polyether sulfonates; polyether-esters such as polybutester; polytetramethylene ether glycol; 1,4-butanediol; polyurethanes; acrylic polymers, copolymers, and resins; modacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polyacrylonitrile; polyvinyl ketones; polyvinyl aromatics such as polystyrene; polyvinyl esters such as polyvinyl acetate; copolymers of vinyl monomers with each other and olefins such as ethylene-methyl methacrylate copolymers, acrylonitrile-styrene copolymers, ABS resins, and ethylene-vinyl acetate copolymers; alkyd resins; polycarbonates and alloys thereof; polyoxymethylenes; polyacetals; polyphosphazine; polysulfones; polymethylpentene; polyimides; epoxy resins; aramids; and combinations thereof.

Alternatively, the plastic material forming member 350 may itself be conductive. Conductive polymers may include, for example, polythiophene, polyacetylene, polyphenylene vinylene, polypyrrole, polyaniline, polyphenylene sulfide, copolymers, and derivatives thereof, among other intrinsically conducting polymers within the purview of those skilled in the art. In embodiments, the conductive polymers may be utilized alone or in combination with conductive filler materials, as described above.

In use, as seen in FIGS. 10-13, the clinician may secure electrode 100 to connector 320 by actuating lever 336 of electrode connector 320 to the second position to enable insertion of press stud 124 of electrode 100 into first slot portion 334a of keyhole slot 334. Thereafter, lever 336 may be released so that biasing member 338 moves cam finger 336a of lever 336 against press stud 124 to push or force press stud 124 into second slot portion 334b of keyhole slot 334. The biasing force of biasing member 338 helps to maintain press stud 124 within second slot portion 334b of keyhole slot 334, and thus inhibits removal or disconnection of the biomedical electrode from connector 320.

Figure 13:
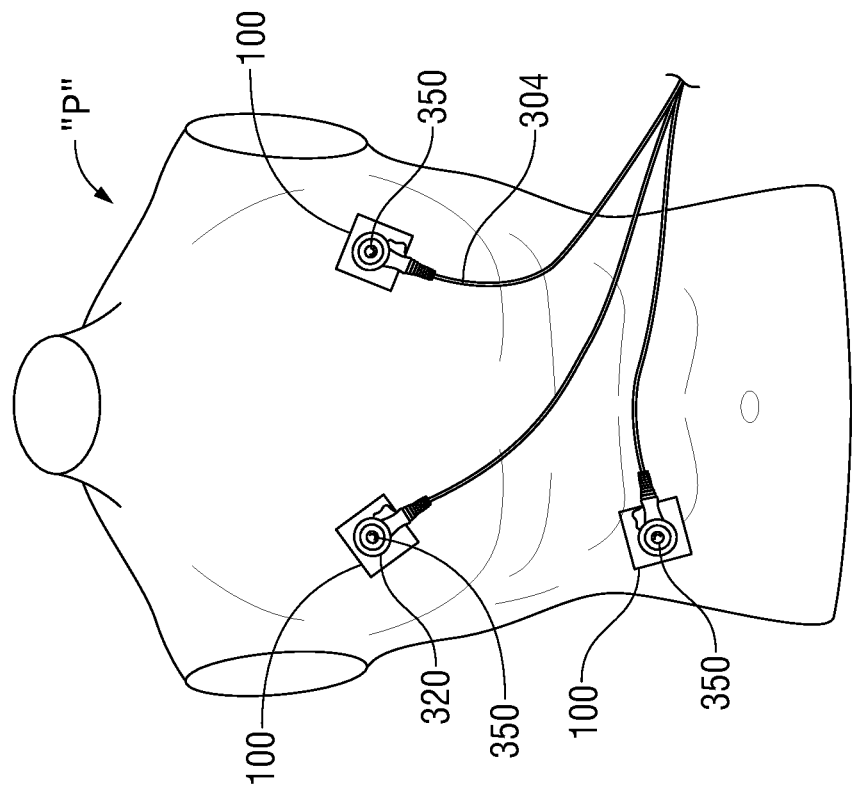
FIGS. 12 and 13 are schematic illustrations of the electrode connectors of FIG. 1 illustrating use thereof.
Figure 12:
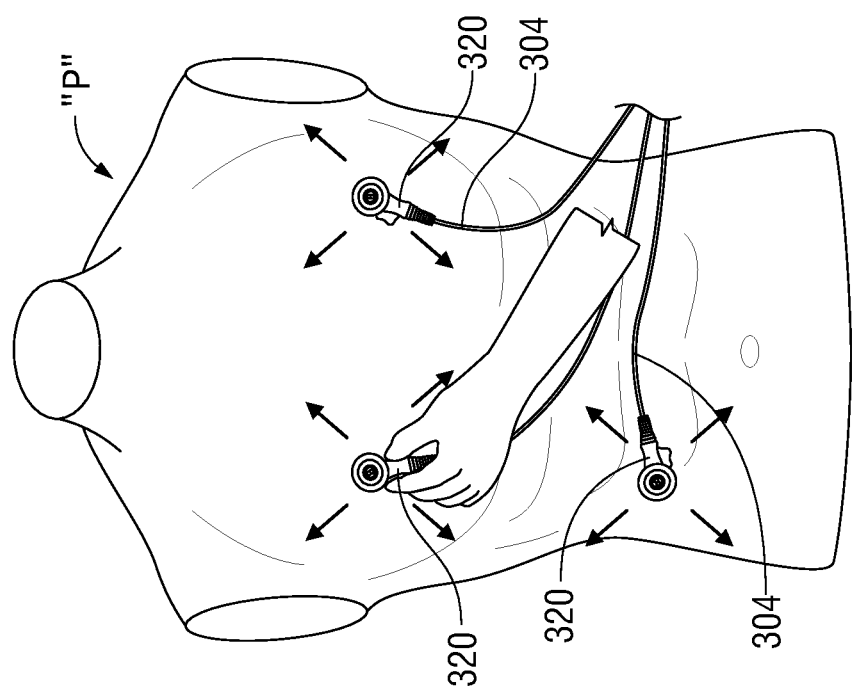

Upon securing electrode 100 with connector 320, the clinician may position electrode connector 320 adjacent the target location on a patient "P." With electrically conductive member 350 in contact with patient "P," the clinician can slidably move electrode connector 320 to a location on patient "P" that provides the strongest signal that will enable a more accurate trace (FIG. 12). Upon determining the desired position on patient "P," the clinician may remove or peel release liner 102, turn electrode connector 320 over, and affix electrode 100 at the desired position on patient "P" (FIG. 13). At this time, the clinician can use floor monitor 2 and/or telemetry monitor 20 to analyze the data obtained thereby. While electrode 100 has been shown to be secured with connector 320 prior to determining the desired location on patient "P," electrode 100 may be secured with connector 320 after determining the desired position on patient "P" or after electrode 100 is affixed to the patient.

Figure 14:
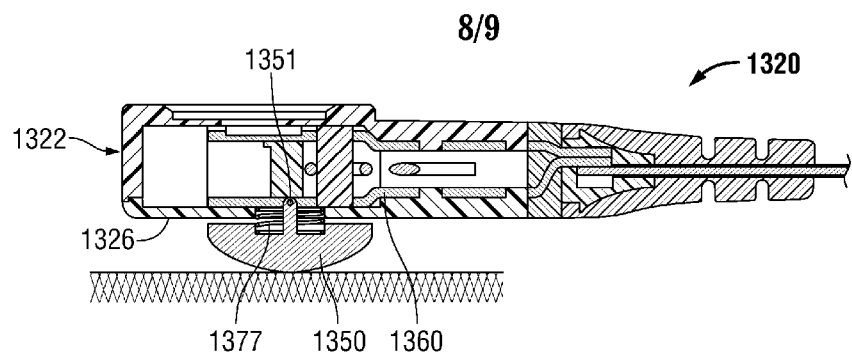
FIGS. 14-16 are side, cross-sectional views of an electrode connector in accordance with another embodiment of the present disclosure.
Figure 15:
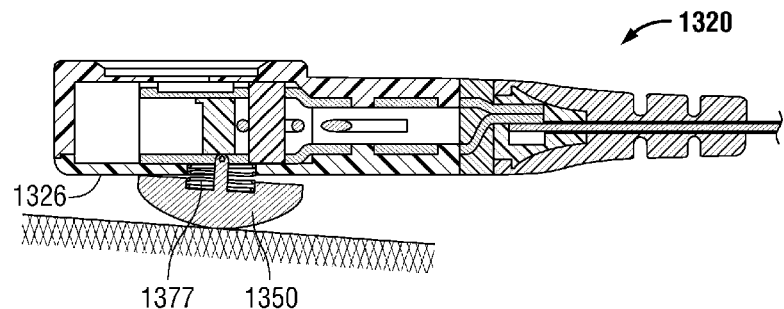
Figure 16:
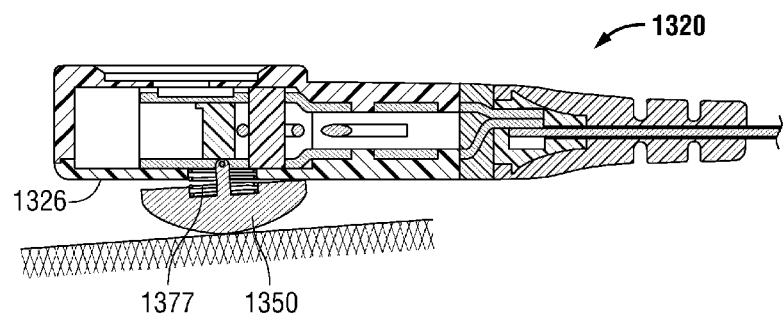

With reference now to FIGS. 14-16, there is provided an electrode connector 1320 in accordance with another embodiment of the present disclosure. The basic structure of electrode connector 1320 is substantially identical to that of connector 320, and thus will not be described in detail herein. In contrast to connector 320, connector 1320 includes an electrically conductive member 1350 that is hingedly connected to a second lead wire terminal 1360 at a hinge 1351. Connector 1320 further includes a biasing member 1377 that enables electrically conductive member 1350 to accommodate the contour of the skin of the patient and to facilitate offset movement of member 1350 with respect to an upper member 1326 of a housing 1322.

Figure 17:
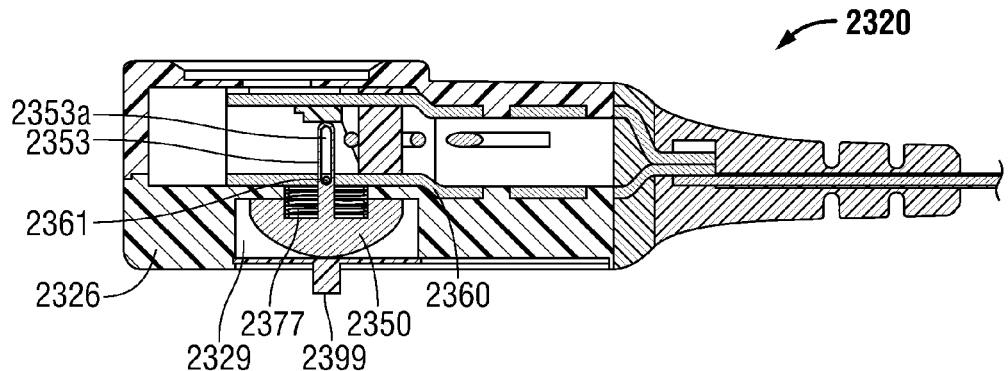
FIGS. 17-19 are side, cross-sectional views of an electrode connector in accordance with yet another embodiment of the present disclosure.
Figure 18:
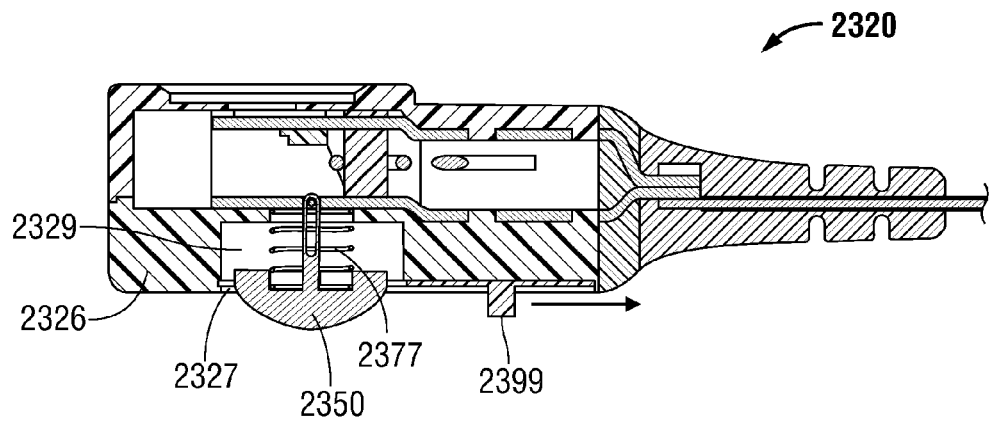
Figure 19:
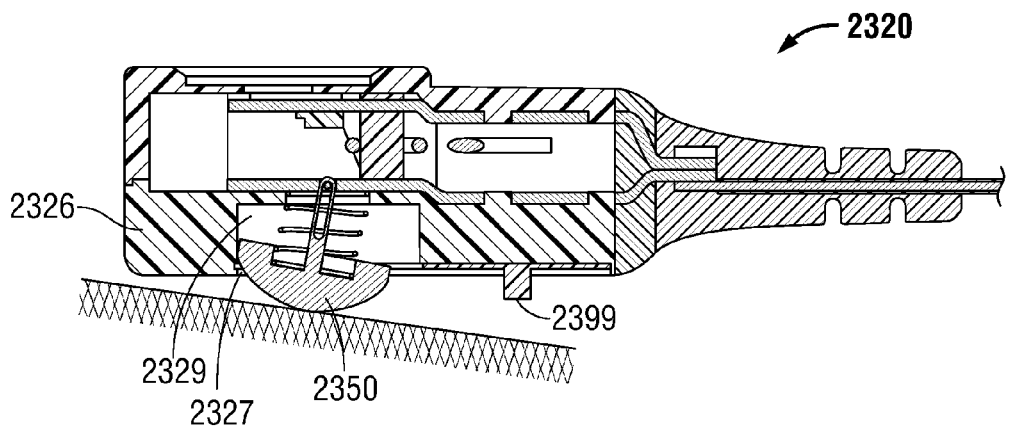

With reference to FIGS. 17-19, there is provided an electrode connector 2320 in accordance with yet another embodiment of the present disclosure. The basic structure of electrode connector 2320 is substantially identical to that of connector 320, and thus will not be described in detail herein. In contrast to connector 320, connector 2320 includes an upper member 2326 having a chamber 2329 defining an opening 2327. Chamber 2329 is configured and dimensioned to receive electrically conductive member 2350 therein. Opening 2327 is provided with a slidable member or door 2399 to open and close opening 2327. In particular, slidable member 2399 and chamber 2329 are made of an insulative material to inhibit inadvertent electrical conduction through member 2350 when member 2350 is disposed in chamber 2329 with slidable member 2399 in the closed position.

Member 2350 includes an arm member 2353 defining a cam slot 2353a. Second lead wire terminal 2360 includes a connector pin 2361 configured and dimensioned to move slidably within cam slot 2353a. Additionally, member 2350 includes a biasing member 2377 to bias member 2350 toward an extended position such that when slidable member 2399 is in the open position, member 2350 extends out of opening 2327. Furthermore, connector slot 2353a in conjunction with biasing member 2377 enables member 2350 to accommodate the contours of the patient when sliding member 2350 on the patient. Moreover, chamber 2329 with the slidable member 2399 inhibits electrical interference by electrically conductive member 2350 when electrode 100 is in use.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An electrode connector comprising:
    a housing defining a first opening configured to receive at least a portion of an electrode therethrough;
    an electrically conductive contact plate defining a bore aligned with the first opening, the bore configured and dimensioned to receive at least a portion of the electrode therein;
    a lead wire terminal electrically connected to the contact plate; and
    an electrically conductive member electrically coupled to the lead wire terminal, the electrically conductive member being supported on the housing and being spaced apart from the first opening, wherein the electrically conductive member is disposed in a second opening defined in the housing, wherein the first and second openings are defined in different sides of the housing.

2. The electrode connector according to claim 1, wherein the electrically conductive member has a hemispherical shape.

3. The electrode connector according to claim 1, wherein the electrically conductive member is hingedly supported within the housing.

4. The electrode connector according to claim 2, wherein the electrically conductive member includes a biasing member to bias the electrically conductive member away from the housing.

5. The electrode connector according to claim 1, wherein the housing defines a chamber configured and dimensioned to receive the electrically conductive member therein.

6. The electrode connector according to claim 5, wherein the chamber includes an opening through which the electrically conductive member extends.

7. The electrode connector according to claim 6, wherein the chamber includes a slidable member movable between open and closed positions to open and close the opening of the chamber.

8. The electrode connector according to claim 7, wherein the slidable member is made of an electrically insulative material.

9. The electrode connector according to claim 1, wherein the electrically conductive member is made of plastic and includes a conductive filler.

10. The electrode connector according to claim 9, wherein the electrically conductive member is made of conductive polymers.

11. The electrode connector according to claim 1, wherein the electrically conductive member protrudes from the housing.

12. The electrode connector according to claim 1, further comprising a lever pivotally coupled to the housing, wherein the lever is pivotable between a first position in which at least a portion of the lever extends across the bore of the contact plate to secure at least a portion of the electrode therein and a second position in which the lever is positioned such that the bore is unobstructed.

13. The electrode connector according to claim 12, wherein the lever further includes a biasing member to bias the lever toward the first position.

14. The electrode connector according to claim 12, wherein the lever further includes a finger configured and adapted to engage the electrode to secure the electrode within the bore of the contact plate when the lever is in the first position.

* * * * *